United States Patent [19]

Bair

[11] Patent Number: 5,643,299
[45] Date of Patent: Jul. 1, 1997

[54] HYDROJET APPARATUS FOR REFRACTIVE SURGERY

[75] Inventor: Scott Bair, Atlanta, Ga.

[73] Assignee: Sentinel Medical, Inc., Orinda, Calif.

[21] Appl. No.: 586,502

[22] Filed: Jan. 16, 1996

[51] Int. Cl.$^6$ ................................................. A61B 17/32
[52] U.S. Cl. ................................................. 606/166; 606/167
[58] Field of Search ................................. 606/166, 167, 606/170–180, 184, 185; 604/19, 22

[56] References Cited

U.S. PATENT DOCUMENTS 5,556,406  9/1996  Gordon et al. .......................... 606/166

*Primary Examiner*—Glenn Dawson
*Attorney, Agent, or Firm*—Harris Zimmerman

[57] ABSTRACT

Apparatus for supporting and guiding the movement of a high speed liquid jet for ophthalmic incisions includes a fixture for removably securing the device with respect to the apex of the cornea. The corneal apex extends through an opening in the fixture, and a concentric suction ring secures the fixture to the eyeball. A proximal portion of the fixture is provided with an internal cutout to permit resilient horizontal flexure of the proximal portion. A first linear actuator is arranged to drive the first flexible bracket to translate horizontally in precisely controlled motion. Joined orthogonally to the fixture is a second flexible bracket, having an internal cutout that permits resilient vertical flexure. One end of the second flexible bracket is secured rigidly to the fixture, and a micrometer actuator is joined to the movable end of the second flexible bracket to position it vertically in precisely controlled spacing. A high pressure liquid jet nozzle extends from the movable end of the second flexible bracket and is directed generally horizontally toward the corneal apex in the opening of the first bracket. A target receptacle is disposed in coaxial alignment with the liquid jet, and connected to a vacuum line to remove the liquid released in the liquid jet. An applanation member extends from a rigid portion of the first flexible bracket to impinge on the corneal apex. The vacuum line is secured to the movable end of the second flexible bracket to move in concert with the cutting jet.

20 Claims, 4 Drawing Sheets

5,643,299

HYDROJET APPARATUS FOR REFRACTIVE SURGERY

BACKGROUND OF THE INVENTION

The present invention relates to hydrojet surgical devices, and more particularly to hydrojet devices used for refractive surgery.

In recent years the use of surgical techniques for correction of ophthalmic refractive malfunction has progressed from experimental laboratory operations to widely accepted, commonplace procedures. Radial keratotomy (RK), photorefractive keratotomy (PRK), and myopic keratomileusis (MKM) have all become routine techniques in ophthalmology. Such aggressive surgical treatment is a relatively new development in ophthalmology. However, many patients require good uncorrected visual acuity for various occupations, such as pilots or professional athletes, and other patients demand good uncorrected visual acuity for cosmetic or psychological reasons. Moreover, some patients have subnormal vision, even when optimally corrected with spectacles or contact lenses, and seek surgical correction for improved vision.

Some photorefractive surgical techniques involve a lamellar keratotomy, in which a hinged flap of apical corneal tissue is created by incision in the cornea generally perpendicular to the primary visual axis. A second cut is then made, in which a thin wafer of stroma is removed. The flap is then returned to its initial position and permitted to heal in place. Removal of the thin wafer of stroma alters the conformation of the corneal apex, thereby modifying the refractive characteristic of the cornea. Clearly, the placement and formation of the second cut, as well as the thickness and planarity of the first incision, are crucial to the success of this technique.

Lamellar keratotomy has been performed using a microkeratome device, in which a high speed rotating cutting head supports a blade that creates the corneal cuts. However, the blade thickness, as well as the mechanical vibration and motion of the moving cutter limits the fineness and planarity of the incisions, which in turn limits the potential for successful outcome of the surgery.

Recently, a high speed water jet has been used in lamellar keratotomy, in a technique termed hydrorefractive keratoplasty (HRK). A water jet having a diameter of 50–100 μm is used to form the corneal incisions. The water jet is far smaller in diameter than the thickness of a cutting blade, whereby the incisions may be much finer, resulting in less tissue trauma, better healing, and greater potential for success. The water jet is a linear "beam" which must be swept through the corneal tissue to effect the necessary incisions. The mechanism to effect the beam movement consists generally of a track on which the water jet nozzle is mounted in slidable fashion. However, it is recognized in mechanical engineering that two slidable surfaces must have a clearance of approximately ±0.001 inch, equal to 25.4 μm. Thus the free play of the sliding mechanism is 25%–50% of the cutting beam diameter, which substantially negates the advantages of using a hydrojet as a fine cutting instrument. The prior art demonstrates a need for an improved mechanism for guiding a hydrojet cutting beam with greater resolution and control.

SUMMARY OF THE INVENTION

The present invention generally comprises an apparatus for supporting and guiding the movement of a high speed liquid jet used for cutting, particularly in the formation of ophthalmic incisions. A salient feature of the apparatus is that it eliminates the mechanical free play of prior art sliding or rolling devices, thereby taking full advantage of the extremely fine cutting beam produced by a high pressure cutting jet, and forming incisions of unprecedented planarity and thinness.

The apparatus includes a fixture for removably securing the device with respect to the apex of the cornea. At the distal end of the fixture, an opening is provided, through which the cornea apex or crown may be extended. Surrounding the opening is a suction ring to secure the fixture to the eyeball with the corneal apex properly positioned in the opening. The distal end portion of the fixture is joined to a lateral bar, which in turn is secured to a rigid horizontal support. The proximal portion of the fixture comprises a first flexible bracket provided with an internal cutout that is fashioned to permit resilient horizontal flexure of the proximal portion while preventing vertical flexure. A first linear actuator is secured to the horizontal support, and the armature of the actuator is connected to the first flexible bracket, whereby the linear actuator may be operated to drive the first flexible bracket to translate horizontally in precisely controlled motion.

Joined orthogonally to the first flexible bracket is a second flexible bracket, which is provided with an internal cutout that permits resilient vertical flexure while preventing horizontal movement. One end of the second flexible bracket is secured rigidly to first flexible bracket, and a second linear actuator is joined to the rigid end of the second flexible bracket. The armature of the second linear actuator is joined to the other, movable end of the second flexible bracket, whereby the linear actuator may be operated to move the second flexible bracket to translate vertically in precise control. The second linear actuator preferably comprises a micrometer, and the armature position may be set with great accuracy to select the thickness of the apical flap formed with the invention.

A high pressure liquid jet nozzle is supported on the movable end of the second flexible bracket and directed generally horizontally toward the corneal apex in the opening of the first bracket. A target receptacle is disposed in coaxial alignment with the liquid jet, and connected to a vacuum line to remove the volume of liquid released in the liquid jet. An applanation member extends from the stationary end of the second flexible bracket, and is adapted to impinge on the corneal apex in closely spaced relationship to the liquid cutting jet. The vacuum line is secured to the movable end of the second flexible bracket, whereby the target receptacle moves in concert with the cutting jet.

The apparatus of the invention is employed by first positioning the first bracket so that the corneal apex extends through the opening thereof, and the suction ring is connected to a low pressure source to secure the device to the eyeball. The applanation member may be formed of a transparent material having a reticle or other scale indicia to determine the proper applanation effect for the procedure to be carried out. The surface of the applanation member that contacts the cornea may be planar or may be provided with a predetermined curvature. In the quiescent disposition, the jet nozzle is aligned so that the liquid jet cannot contact the corneal tissue.

The liquid jet is then activated, creating a fine beam of extremely high velocity liquid extending from the nozzle to the target receptacle. The first linear actuator is then activated to translate the nozzle horizontally by bending the first flexible bracket, whereby the liquid jet beam is translated horizontally through the corneal tissue. Due to the fact that the diameter of the cutting jet is 50 μm or less, and that there is no free play in the mechanism that translates the cutting jet, the incision in the cornea is extremely planar and very thin. Thus the incision is very smooth and removes an absolute minimum of tissue, so that rapid healing is promoted and refractive characteristics are precisely controlled.

The micrometer may be actuated as required to set the vertical position of the incision and determine the thickness of the apical flap. Thus the apparatus may direct the cutting jet to perform all the incisions required for MKM or HRK. Conversely, the apparatus may be used only to carry out the first planar incision which forms the anterior apical corneal flap, setting the stage for the stromal resection step which may be carried out by other surgical means.

DESCRIPTION OF THE PREFERRED EMBODIMENT

Figure 1:
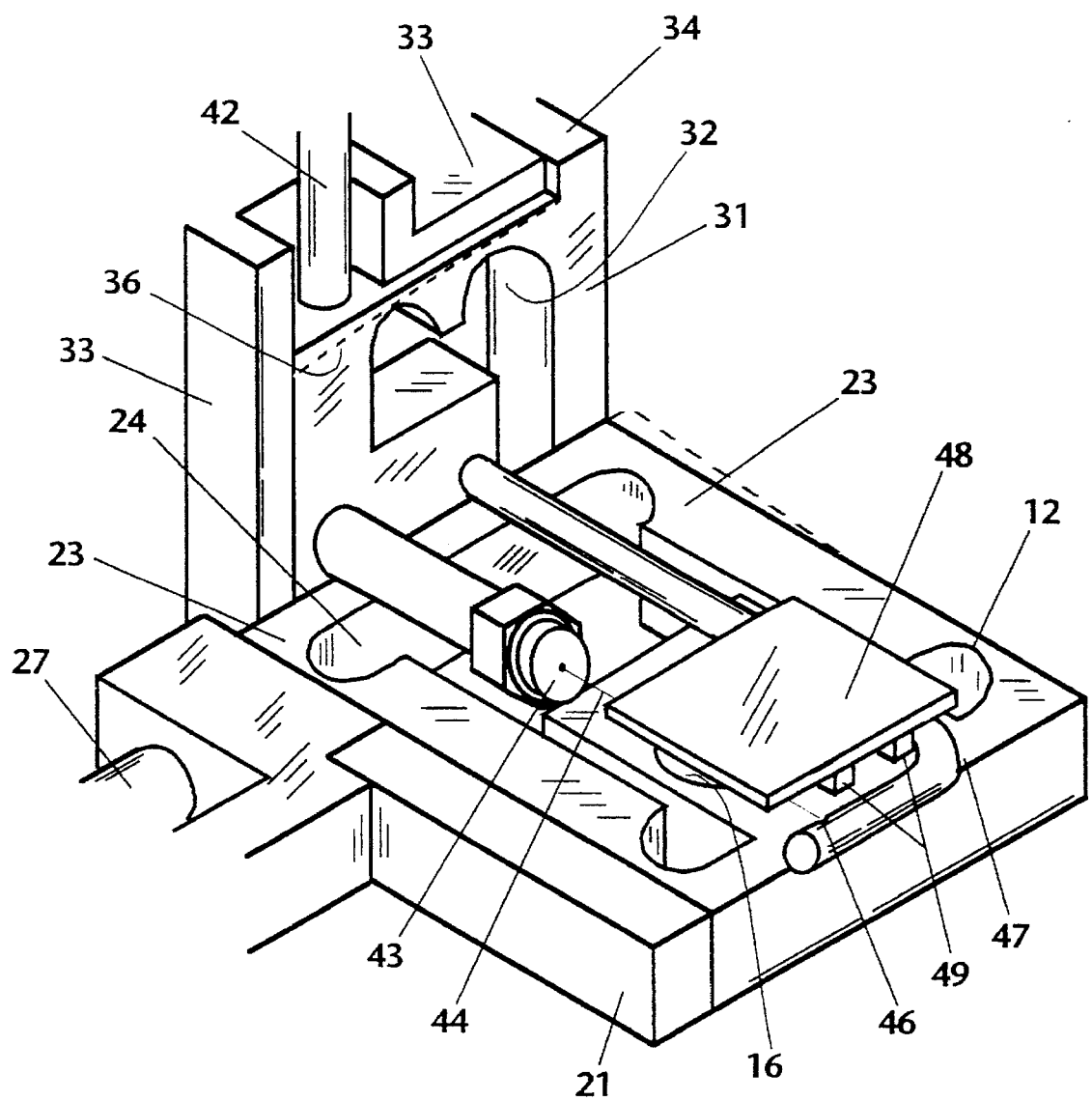
FIG. 1 is a perspective view of the apparatus for supporting and directing a liquid cutting jet for refractive surgery.
Figure 2:
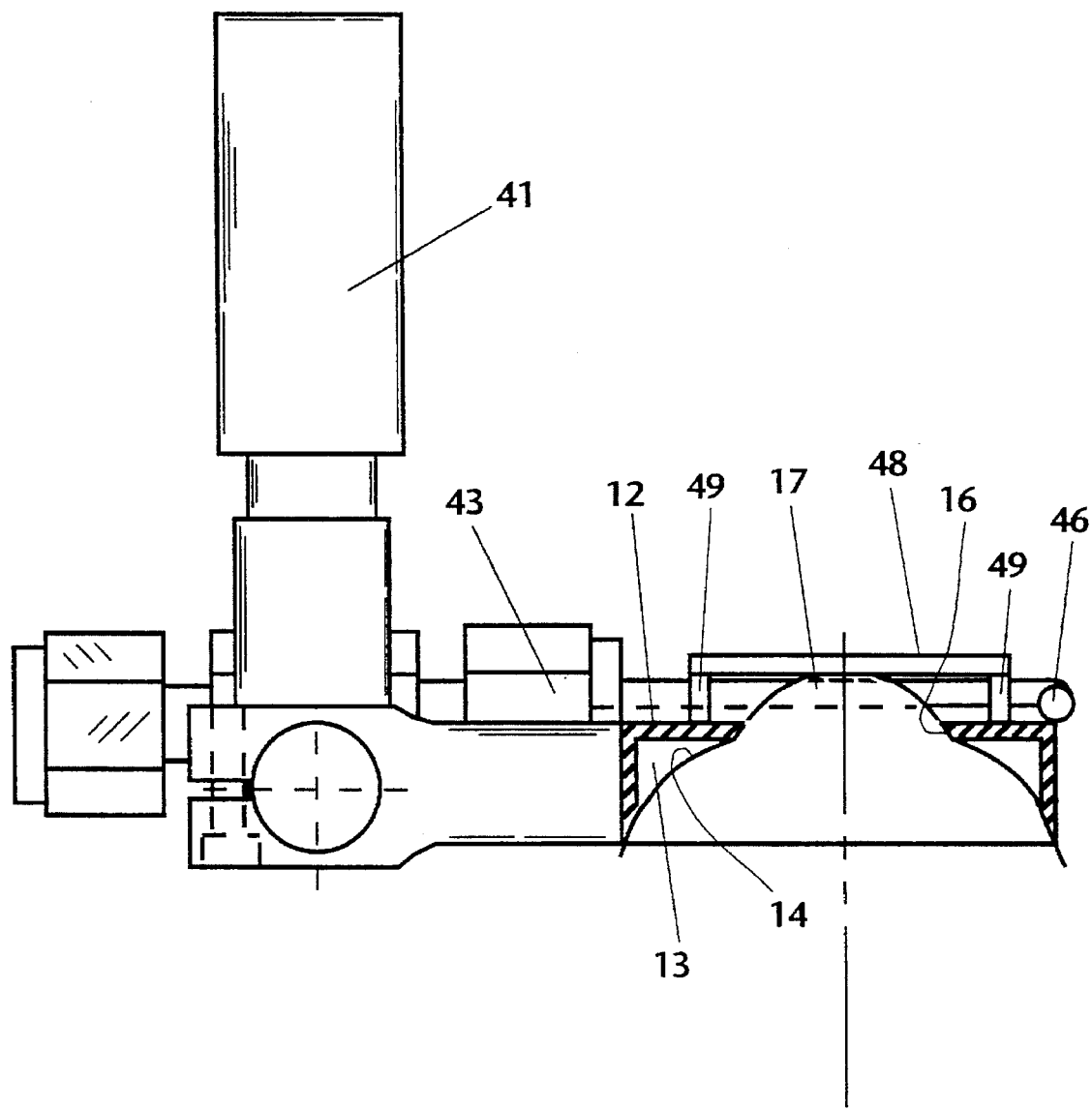
FIG. 2 is a side view of the apparatus shown in FIG. 1 for supporting and directing a liquid cutting jet for refractive surgery.
Figure 3:
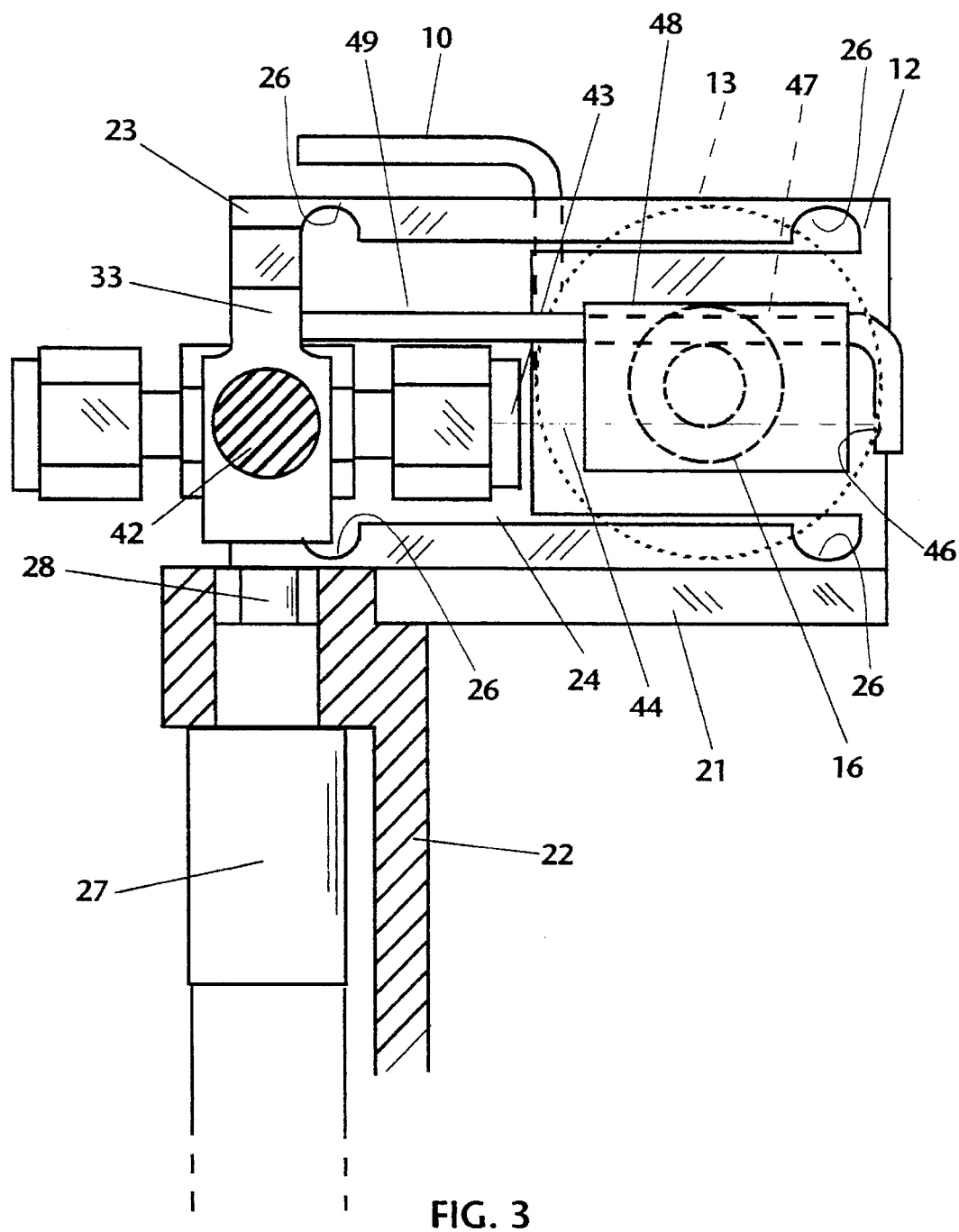
FIG. 3 is a partially cutaway top view of the apparatus shown in FIGS. 1 and 2 for supporting and directing a liquid cutting jet for refractive surgery.
Figure 4:
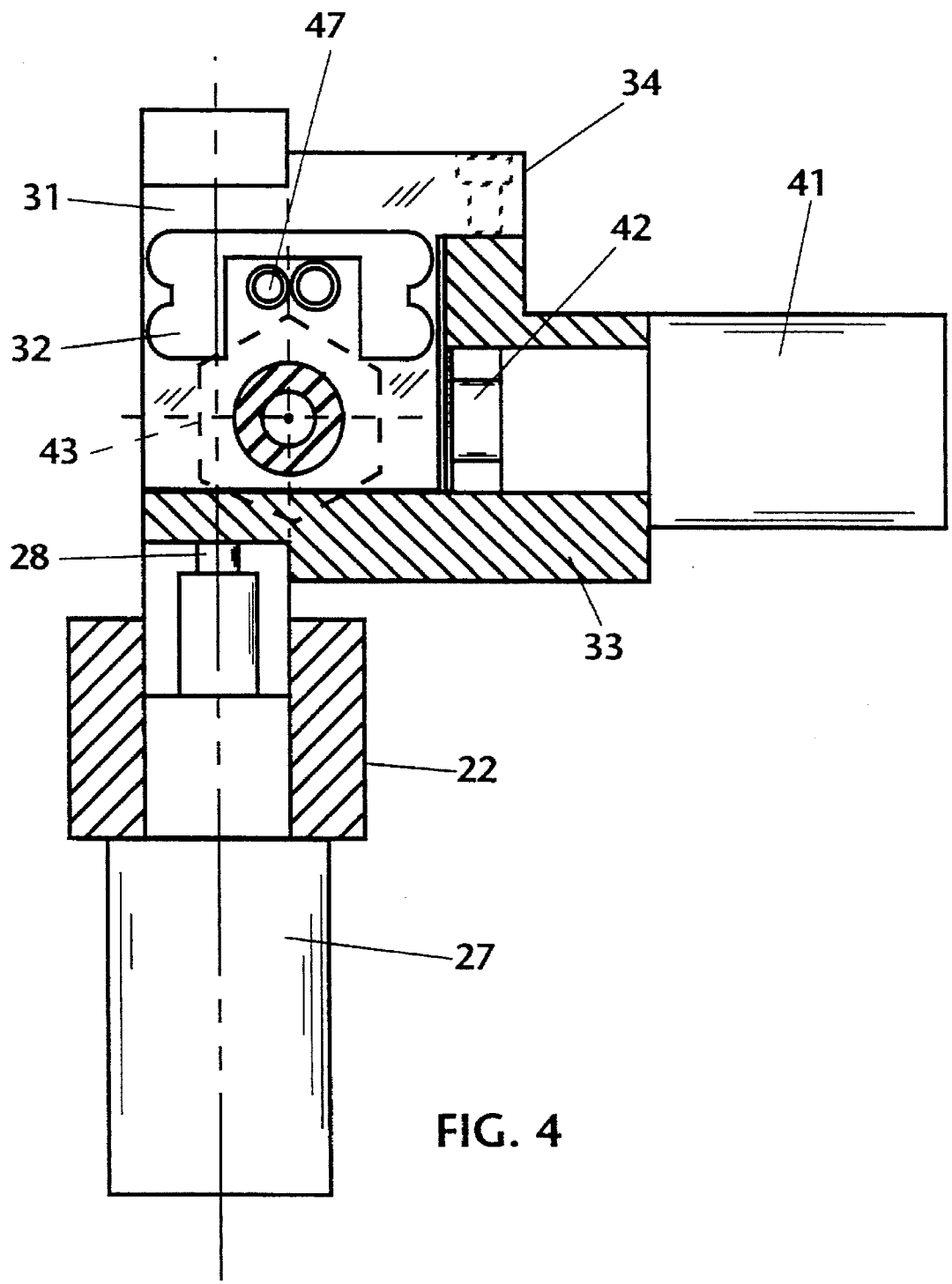
FIG. 4 is a partially cutaway end view of the apparatus shown in FIGS. 1–3 for supporting and directing a liquid cutting jet for refractive surgery.

The present invention generally comprises an apparatus for supporting and guiding the movement of a high speed liquid jet used for cutting, particularly in the formation of ophthalmic incisions. With regard to the accompanying FIGS. 1–4, the apparatus 11 includes a plate-like fixture 12 adapted to engage the anterior surface 14 of the eye. The lower surface of the fixture is provided with a suction ring 13 for receiving and releasably securing the anterior surface 14. A supply tube 10 extends to the suction ring to provide a low pressure source and adhere the suction ring to the eyeball when required. An aperture 16 extends through the upper surface of the fixture to communicate with the suction ring in coaxial alignment, the aperture 16 being dimensioned to permit the corneal crown or apex 17 to extend upwardly therethrough. The fixture 12 thus defines the surgical site for corneal refractive or therapeutic procedures, and further provides support and guidance for the hydrojet cutting instrument in a fixed relationship with respect to the corneal apex, as described below.

The fixture 12 is joined rigidly to a lateral bar 21, which is secured to a horizontal support 22 extending from a stable base structure (not shown). The proximal end portion 23 of the fixture 12 comprises a first flexible bracket that is free of attachment to the horizontal support 22 or support bar 21. An internal opening 24 is disposed in the portion 23. The opening 24 is a quadrilateral having projecting rounded corners that define thin sidewall portions 26. The thin sidewall portions 26 are resiliently flexible in the horizontal plane (the nominal plane of the fixture 12); however, due to the vertical thickness of the structure, the sidewall portions 26 are highly resistant to vertical flexure. Thus the conformation of the opening 24 permits the first flexible bracket 23 to translate horizontally with respect to the rigidly supported end of the fixture 12.

Secured to the horizontal support 22 is a horizontal linear actuator 27. The armature 28 of the linear actuator 27 is coupled to the proximal end portion 23 of the fixture, whereby operation of the actuator 27 drives the portion 23 to translate horizontally. This translational motion may be controlled with great precision, as there is no sliding or rolling surface contact required to effect the motion.

Extending generally orthogonally from the first flexible bracket 23 a second plate-like flexible bracket 31. The bracket 31 is provided with an internal opening 32 similar in conformation and function to the opening 24, whereby the bracket 31 is capable of resilient bending in the vertical plane while exhibiting high rigidity in the horizontal plane. A rigid support bracket 33 is secured to the movable portion 23 of the first flexible bracket to extend generally vertically therefrom. One edge 34 of the second flexible bracket 31 is secured to a portion of the bracket 33, while the opposed end portion 36 is free to translate vertically in bending fashion.

Secured to the rigid support bracket 33 is a vertical linear actuator 41. The armature 42 of the linear actuator 41 is coupled to the end portion 36 of the second flexible bracket 31. Operation of the linear actuator 41 drives the end portion 36 to translate vertically in resilient bending motion. This translational motion may be controlled with great precision, as there is no sliding or rolling surface contact required to effect the motion. The vertical linear actuator preferably comprises a micrometer, so that the vertical position of the jet nozzle and thus the thickness of the apical flap formed by the mechanism may be selected with extremely high precision.

A high pressure liquid jet nozzle 43 is supported on the movable end 36 of the second flexible bracket 31. The liquid jet 44 is directed generally horizontally toward the corneal apex in the opening 17 of the fixture 12. A target receptacle 46 is disposed in coaxial alignment with the liquid jet 44, and connected to a vacuum line 47 to remove the volume of liquid released in the liquid jet. The vacuum line 47 extends from the movable end 36 of the second flexible bracket 31, so that the target receptacle moves in concert with the liquid jet to intercept the jet as the jet is directed by the vertical and horizontal linear actuators.

The apparatus also provides an applanation member 48, comprising a planar tabular member disposed to impinge on the apical surface of the cornea presented in the opening 16. The applanation member 48 is supported by standoffs 49 on the fixed portion of the fixture 12. The planar member 48 is closely spaced in the vertical direction to the liquid jet 44, and is stationary with respect to the liquid jet to maintain a relatively constant spacing therefrom.

The jet nozzle 43 is connected to a source of very high pressure liquid, and is designed to generate a liquid jet having extremely high velocity and a diameter of 50 μm or less. The jet defines a cutting beam that exhibits no significant increase in diameter in the distance it travels to the target receptacle, and the cutting beam severs the interposed corneal tissue with ease. The apparatus 11 is employed by first positioning the first bracket so that the corneal apex 17 extends through the opening 16, and the suction ring 13 is actuated to secure the device to the eyeball. The applanation member 48 may be formed of a transparent material having a reticle or other scale indicia to determine the proper applanation effect for the procedure to be carried out. The surface of the applanation member 48 that contacts the apex 17 may be planar or may be provided with a predetermined curvature. It the quiescent disposition, the jet nozzle is aligned so that the liquid jet cannot contact the corneal tissue.

The liquid jet 44 is then initiated, creating the beam of extremely high velocity liquid extending from the nozzle 43 to the target receptacle 46. The first linear actuator 27 is then activated to translate the nozzle 43 horizontally by bending the first flexible bracket 23, whereby the liquid jet beam is translated horizontally through the corneal tissue. Due to the fact that the diameter of the cutting jet is 50 μm or less, and that there is no free play in the mechanism that translates the cutting jet, the incision in the cornea is extremely planar and very thin. That is, the flexure mechanism of the apparatus takes maximum advantage of the extremely fine cutting capability of the liquid jet. Thus the incision is very smooth and removes an absolute minimum of tissue, so that rapid healing is promoted and refractive characteristics are precisely controlled.

The second linear actuator 41 may be actuated as required to set the vertical position of the incision, and this vertical position determines the thickness (vertical depth) of the apical flap formed by the invention. It is noted that the vertical deflection mechanism formed by the brackets 31 and 32 and actuator 41 is supported entirely on the horizontal deflection mechanism, whereby the position of the jet nozzle 43 is a summation of the vertical and horizontal translations effected by the apparatus 11.

The apparatus 11 may direct the cutting jet 44 to perform all the incisions required for MKM, HRK, ALK, or the like. Conversely, the apparatus may be used only to carry out the first planar incision which forms the anterior apical corneal flap, setting the stage for the stromal resection step which may be carried out by other surgical means.

It is noted that the incisions formed by the apparatus 11 may be carried out not only with extreme precision, but with extreme rapidity. The formation of an apical corneal flap may require only approximately 1–5 seconds, and a stromal resection incision may require approximately the same amount of time.

The foregoing description of the preferred embodiment of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

I claim:

1. An ophthalmic surgical device, comprising:
   fixture means for releasably engaging an anterior surface portion of an eye;
   liquid jet nozzle means for generating a high velocity liquid jet capable of cutting eye tissue;
   bending means extending from said fixture means for undergoing translational flexure without sliding contact;
   said liquid jet nozzle means extending from said bending means; and,
   precision actuator means coupled to said bending means to flexibly translate said bending means and direct said high velocity liquid jet in cutting the eye tissue engaged in said fixture means.

2. The ophthalmic surgical device of claim 1, wherein said fixture means includes an aperture dimensioned to receive the corneal apex of an eye extending therethrough.

3. The ophthalmic surgical device of claim 2, wherein said fixture includes a suction ring disposed concentrically with respect to said aperture to releasably engage the anterior eye surface surrounding the corneal apex.

4. The ophthalmic surgical device of claim 1, wherein said bending means includes a first flexible bracket extending from said fixture means.

5. The ophthalmic surgical device of claim 4, wherein said first flexible bracket comprises a first plate-like member extending in a first plane, and further including an interior opening formed in said plate-like member and extending through said first plane.

6. The ophthalmic surgical device of claim 5, wherein said interior opening defines a plurality of thin sidewall sections in said first plate-like member, said thin sidewall sections characterized by resiliently bending readily in said first plane and strongly resisting bending out of said first plane.

7. The ophthalmic surgical device of claim 6, wherein said precision actuator means includes a first linear actuator secured to said fixture means, said linear actuator including a movable armature coupled to said first flexible bracket to bend and translate said first flexible bracket in said first plane.

8. The ophthalmic surgical device of claim 7, further including a second flexible bracket operatively connected to said first flexible bracket.

9. The ophthalmic surgical device of claim 8, wherein said second flexible bracket comprises a second plate-like member extending in a second plane, and further including an interior opening formed in said second plate-like member and extending through said second plane.

10. The ophthalmic surgical device of claim 9, wherein said second plane intersects said first plane.

11. The ophthalmic surgical device of claim 10, wherein said interior opening defines a plurality of thin sidewall sections in said second plate-like member, said thin sidewall sections characterized by resiliently bending readily in said second plane and strongly resisting bending out of said second plane.

12. The ophthalmic surgical device of claim 11, wherein said precision actuator means includes a second linear actuator secured to said first flexible bracket means, said second linear actuator including a movable armature coupled to said second flexible bracket to bend and translate said second flexible bracket in said second plane.

13. The ophthalmic surgical device of claim 12, wherein said liquid jet nozzle means is secured to said second flexible bracket means and configured to be directed proximate to the anterior surface portion of the eye engaged in said fixture means, whereby translational bending motions of said first and second flexible brackets are imparted to said liquid jet nozzle means in additive fashion.

14. The ophthalmic surgical device of claim 13, further including target receptacle means supported on said second flexible bracket in spaced apart relationship to said liquid jet nozzle means and disposed to receive said high velocity liquid jet.

15. The ophthalmic surgical device of claim 1, further including applanation means for impinging on the anterior surface portion of the eye engaged in said fixture means and imparting a predetermined conformal surface to the corneal apex of the eye.

16. The ophthalmic surgical device of claim 15, further including standoff means extending from said fixture means for supporting said applanation means in fixed relationship to the anterior surface portion of the eye engaged in said device.

17. The ophthalmic surgical device of claim 16, wherein said applanation means includes a planar surface disposed to impinge on the anterior surface portion of the eye engaged in said device.

18. The ophthalmic surgical device of claim 13, wherein said second linear actuator comprises a micrometer for precisely positioning said liquid jet nozzle with respect to the plane of said first flexible bracket.

19. A method for surgical treatment of a eye, comprising the steps of:

providing a fixture and removably securing the fixture to the anterior surface of the eye;

joining a flexible bracket assembly to the fixture, and supporting a liquid jet nozzle on the flexible bracket assembly;

joining a precision linear actuator to the fixture to engage the flexible bracket assembly and selectively bend the flexible bracket assembly;

supplying high pressure liquid to the liquid jet nozzle to generate a high velocity jet;

operating the precision linear actuator to bend the flexible bracket assembly and translate the liquid jet nozzle to translate the high velocity jet through the eye tissue and form an incision.

20. The method of claim 19, further including the step of impinging a nonmovable applanation member on the anterior surface of the eye prior to supplying high pressure liquid to the liquid jet nozzle, and thereafter translating the high velocity jet through the eye tissue in a plane parallel to said applanation member and spaced apart therefrom by a precisely predetermined dimension.

* * * * *